US009073419B2

(12) United States Patent
Pfertner et al.

(10) Patent No.: US 9,073,419 B2
(45) Date of Patent: Jul. 7, 2015

(54) WIND DEFLECTOR

(71) Applicant: Dr. Ing. h.c. F. Porsche Aktiengesellschaft, Stuttgart (DE)

(72) Inventors: Kurt Pfertner, Friolzheim (DE); Markus Alexander Bauer, Heusenstamm (DE)

(73) Assignee: Dr. Ing. h.c.F. Porsche Aktiengesellschaft (DE)

( * ) Notice: Subject to any disclaimer, the term of this patent is extended or adjusted under 35 U.S.C. 154(b) by 0 days.

(21) Appl. No.: 14/472,694

(22) Filed: Aug. 29, 2014

(65) Prior Publication Data

US 2015/0076870 A1 Mar. 19, 2015

(30) Foreign Application Priority Data

Sep. 16, 2013 (DE) .................... 10 2013 110 143

(51) Int. Cl.
*B60J 7/043* (2006.01)
*B60J 7/22* (2006.01)
(52) U.S. Cl.
CPC ......................... *B60J 7/22* (2013.01)
(58) Field of Classification Search
CPC ............................................. B60J 7/22
See application file for complete search history.

(56) References Cited

U.S. PATENT DOCUMENTS

| 2,991,094 | A | * | 7/1961 | Voigtmann et al. | ........... 403/107 |
| 4,026,595 | A | * | 5/1977 | Jacks | ......... 296/180.3 |
| 4,170,378 | A | * | 10/1979 | Jacobsen | ................ 296/180.4 |
| 4,681,364 | A | * | 7/1987 | Bienert et al. | ............. 296/217 |
| 6,523,889 | B2 | | 2/2003 | Birndorfer et al. | |
| 2009/0001773 | A1 | * | 1/2009 | Leopold | ..................... 296/217 |

FOREIGN PATENT DOCUMENTS

DE 3932739 4/1991
DE 102004050513 3/2006

* cited by examiner

*Primary Examiner* — Lori L Lyjak
(74) *Attorney, Agent, or Firm* — Gerald E. Hespos; Michael J. Porco; Matthew T. Hespos

(57) ABSTRACT

A wind deflector has a bearing base and a shiftable body that is shiftable relative to the bearing base between a first, extended position, in which the body is spaced apart from the bearing base and a second, placed-on position, in which the body is placed onto the bearing base. Two spaced apart links extend between the body and the bearing base. Each link has one end articulated to the body and a second end articulated to the bearing base. A push-push lock is provided for fixing at least one of the link and the body in the placed-on position of the body.

7 Claims, 7 Drawing Sheets

WIND DEFLECTOR

CROSS-REFERENCE TO RELATED APPLICATION

This application claims priority under 35 USC 119 to German Patent Application No. 10 2013 110 143.7 file on Sep. 16, 2013, the entire disclosure of which is incorporated herein by reference.

BACKGROUND OF THE INVENTION

1. Field of the Invention

The invention relates to a wind deflector, in particular for a front edge of a roof opening in a motor vehicle.

2. Description of the Related Art

Roof openings of sliding roofs or convertible roofs cause noises when open due to the air flowing in at the roof opening. These noises are perceived as being unpleasant.

Wind deflectors that extend on the front edge of the roof opening and into the air flow have been disclosed to reduce the production of noise. In this context, DE 39 32 739 A1 discloses a wind deflector that is erected automatically in a spring-loaded manner when the roof opening is opened. DE 10 2004 050 513 B3 discloses a wind deflector with a special locking mechanism that can be actuated manually so that the wind deflector can be erected. U.S. Pat. No. 6,523,889 discloses a wind deflector with an electric motor drive.

Automatically erectable wind deflectors are of simple construction. However, they have the disadvantage of always being erected when the roof opening is opened. By contrast, wind deflectors with a locking mechanism are more complicated, but can be erected individually.

An object of the invention to provide a wind deflector that is erectable individually and is nevertheless of simple and cost-effective construction.

SUMMARY OF THE INVENTION

The invention relates to a wind deflector with a shiftable body and a bearing base. The body is shiftable relative to the bearing base so that the body can take up a first, extended position, in which the body is spaced from the bearing base, and a second, placed-on position, in which the body is placed onto the bearing base. Two spaced apart links are provided between the body and the bearing base. A first end of each link is articulated to the body and a second end of each link is articulated to the bearing base. A locking means is provided for fixing at least one link and/or the body in the placed-on position of the body. The locking means is designed as a push-push locking means.

The locking means may comprise a cardioid and an engagement means for engaging in the cardioid.

The cardioid or the engagement means may shiftable.

In one embodiment, the cardioid may be fixed positionally, and the engagement means may be pivotable on the link and/or the body.

In a further embodiment, the cardioid may be laterally shiftable, and the engagement means may be fixed positionally on the link and/or on the body.

A spring may be braced between the bearing base and at least one link and loads the body into the extended position.

An adjustable stop may be provided on the bearing base to limit the movement of at least one link in the extended position.

The invention is explained in detail below using an exemplary embodiment with reference to the drawings.

DETAILED DESCRIPTION

Figure 1:
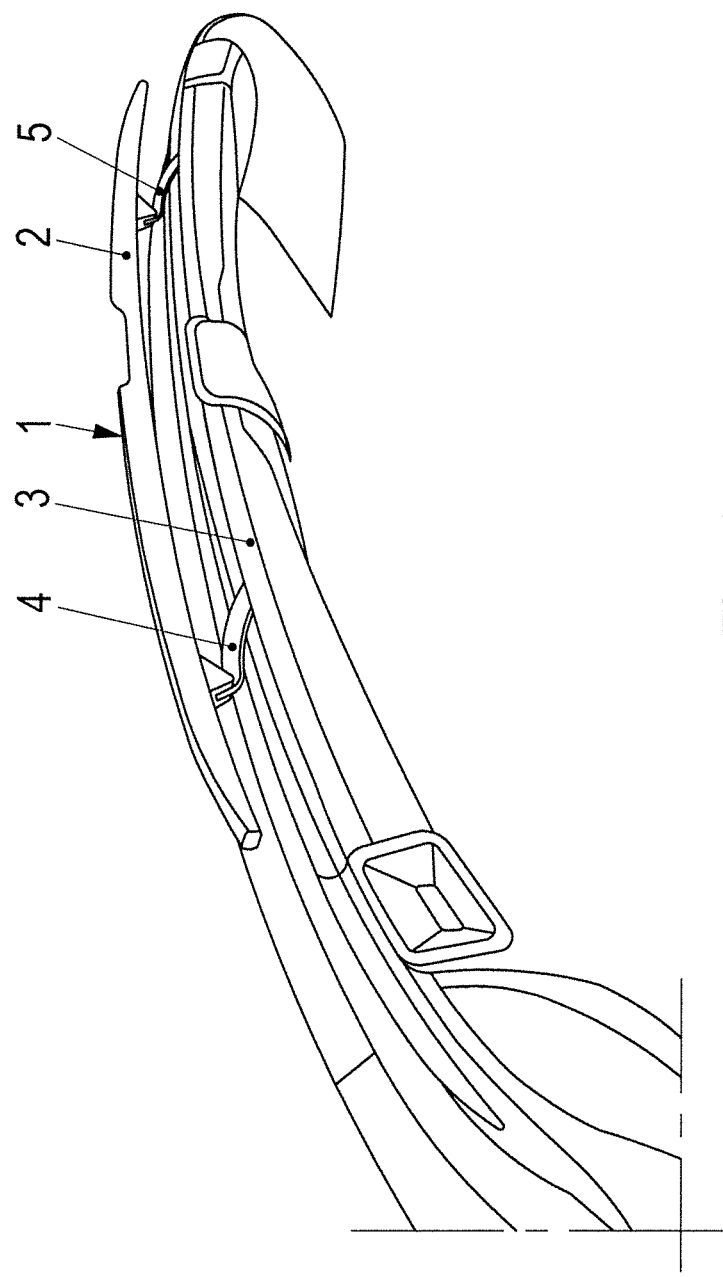
FIG. 1 is a view of a wind deflector of the invention on a cowl frame of a roof opening in a motor vehicle.

FIG. 1 shows a wind deflector 1 arranged on a front edge of a roof opening in a motor vehicle. The wind deflector 1 has a shiftable body 2 and a bearing base 3. The bearing base 3 is arranged on the front edge of the roof opening, or on a windshield frame and/or on a cowl. The bearing base may also be formed integrally with the windshield frame and/or a cowl.

Links 4, 5 are arranged between the body 2 and the bearing base 3 for shifting the body 2 relative to the bearing base 3. For this purpose, the links 4, 5 are connected in an articulated manner at the respective end regions thereof to the body 2 and in an articulated manner to the bearing base 3.

FIG. 1 shows the body 2 in a first, extended position where the body 2 is spaced from the bearing base 3 so that air can flow in between the body 2 and the bearing base 3. The body 2 also can take up a second, placed-on position, in which the body is substantially placed onto the bearing base 3.

The links 4, 5 are spaced apart from each other in the lateral direction with respect to the body 2 and have substantially the same orientation so that the links 4, 5 are substantially parallel to each other.

The body 2 and the bearing base 3 also are arranged substantially parallel to each other. Arranged substantially parallel to each other here does not necessarily mean the arrangement of two rectilinear elements that are parallel to each other, but also possibly two curved elements that have a comparable curvature and the same orientation.

A locking means may be provided, but is not illustrated in FIG. 1. The locking means permits, preferably in a push-push locking manner, the locking of the body 2 to the bearing base 3 in the second, placed-on position.

As shown in FIG. 1, the body 2 has a substantially arcuate or bow-like shape, wherein a constriction in the height of the body 2 is provided, as viewed in the lateral direction in the central region.

Figure 2:
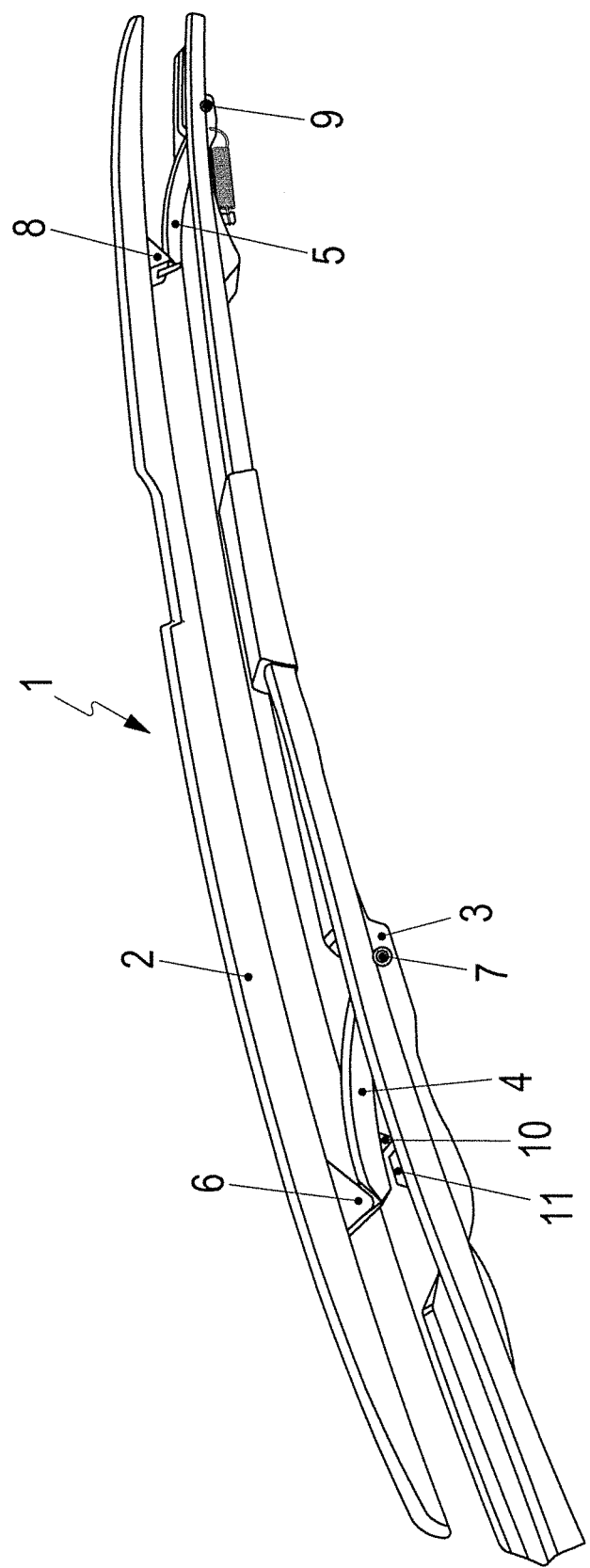
FIG. 2 is a view of a wind deflector on a cowl frame of a roof opening in a motor vehicle.

FIG. 2 is an enlarged illustration of the wind deflector 1 of FIG. 1 and shows the links 4, 5 connected in an articulated manner to the bearing base 3 and to the shiftable bodies 2 at bearings 6, 7, 8, 9. A locking element 10 is provided on the link 4 and interacts with a second locking element 11 within the bearing base 3 to form a locking means. The locking element 10 meshes with the locking means 11 and brings about a push-push lock.

A locking element or locking means preferably is not provided on the link 5, since it is generally sufficient if a locking means is provided on the link 4 arranged on the driver's side.

Figure 3:
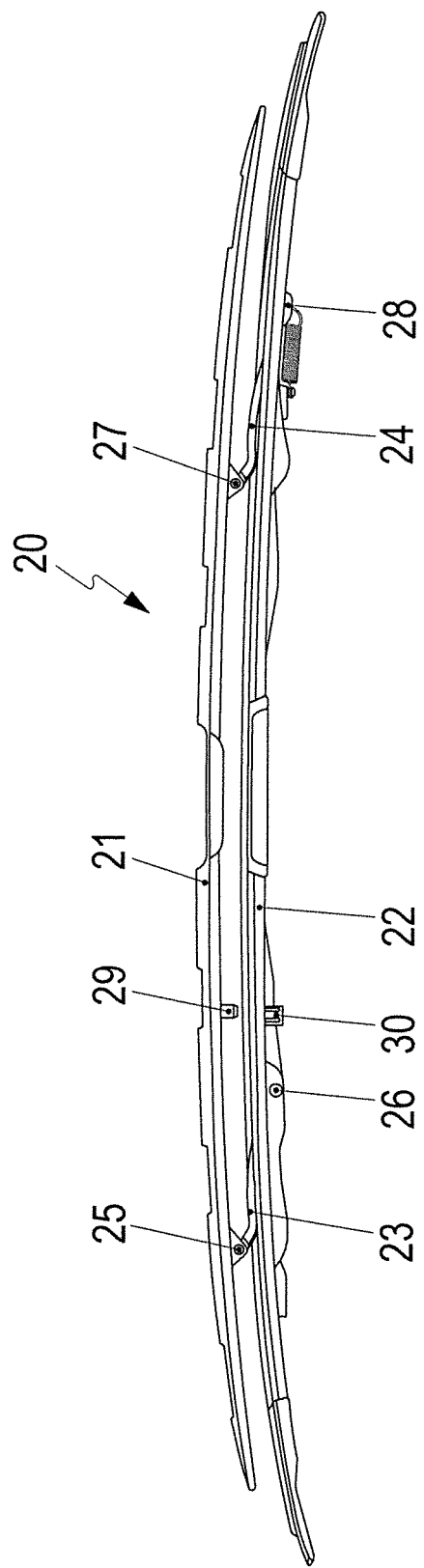
FIG. 3 is a view of a wind deflector according to a second embodiment of the invention on a cowl frame of a roof opening in a motor vehicle.

FIG. 3 shows an alternative configuration of a wind deflector 20 with a shiftable body 21 and a bearing base 22 and with links 23, 24 connected in an articulated manner at the coupling points 25, 26, 27, 28 to be able to pivot the shiftable body 21 relative to the bearing base 22. The embodiment of FIG. 3 has a locking element 29 on the shiftable body 21 and a second locking element 30 on the bearing base 22. The two locking elements 29, 30 are designed as a push-push locking means and interact with each other in the second, placed-on position to bring about a push-push lock.

Figure 4:
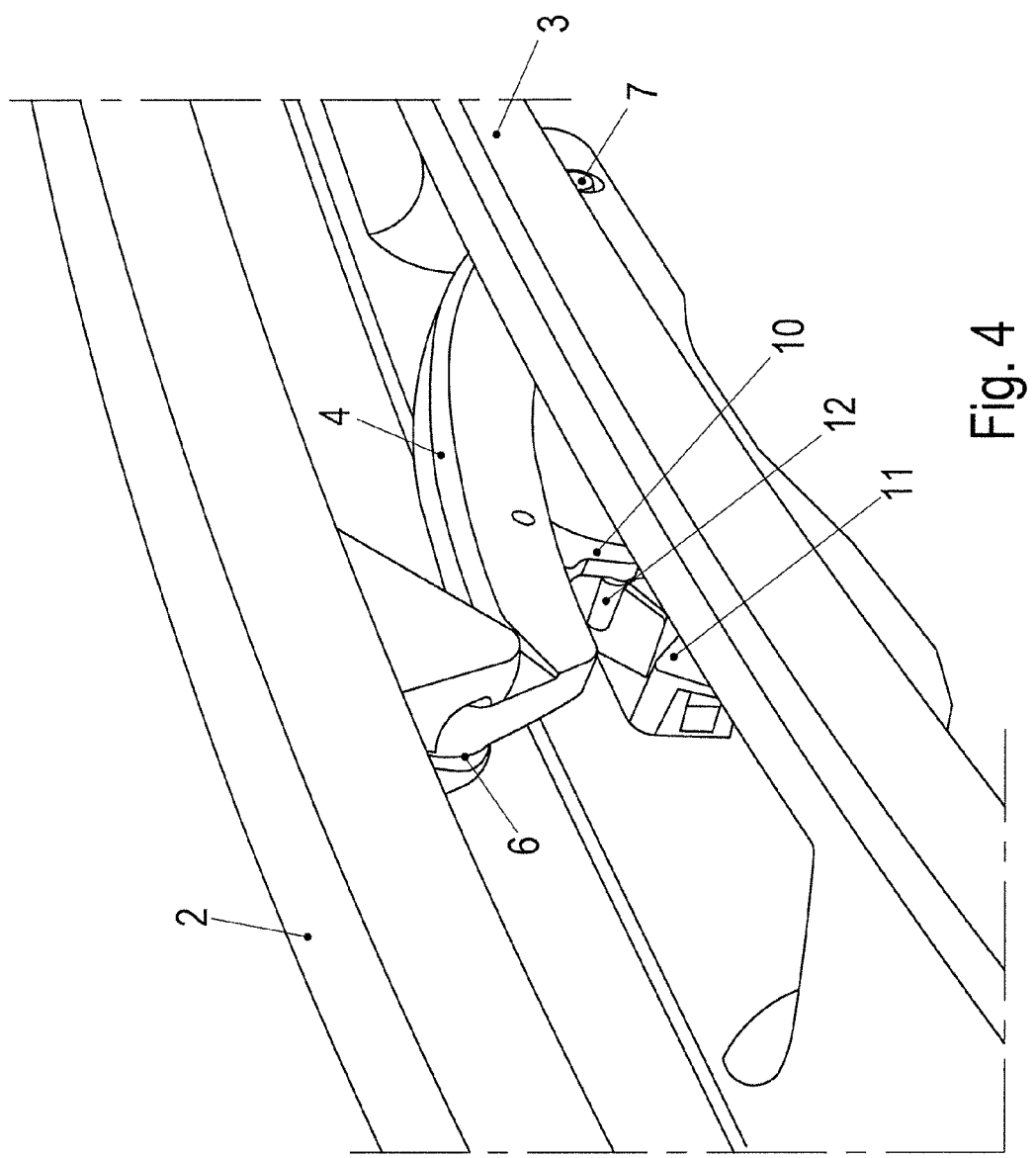
FIG. 4 is a view of a cutout of a wind deflector with a link between the body and the bearing base.

FIG. 4 is a cutout from FIG. 2 that shows the shiftable body 2, the bearing base 3 and the link 4. The link 4 is connected pivotably in an articulated manner to the shiftable body 2 and the bearing base 3 at the coupling means 6 and at the coupling means 7. The locking element 11 is a cardioid arranged within the bearing base 3 and the locking element 10 has a hook 12 arranged in an articulated manner on the link 4. The hook 12 of the locking element 10 can engage the cardioid of the locking element 11 to secure the link 4 and therefore also the body 2 relative to the bearing base 3.

Figure 5:
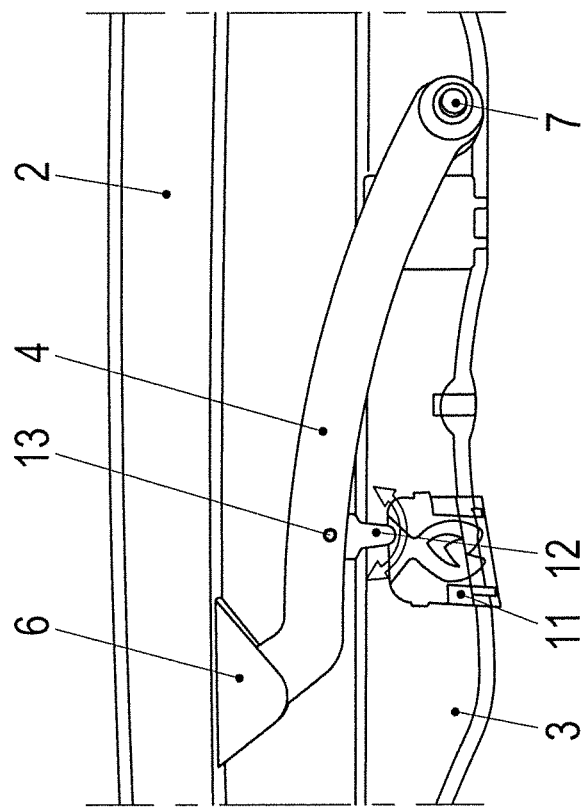
FIG. 5 is a view of a cutout of a wind deflector with a link between the body and the bearing base.
Figure 6:
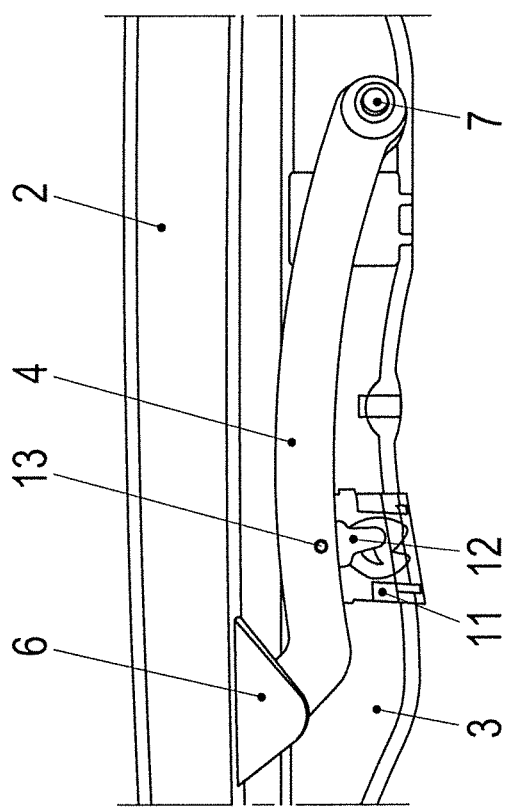
FIG. 6 is a view of a cutout of a wind deflector with a link between the body and the bearing base.

FIGS. 5 and 6 schematically illustrate the arrangement and manner of operation of the locking elements 10, 11 relative to the bearing base 3 and to the shiftable body 2. The element 11 constitutes a cardioid in a cassette in which the hook 12 can engage from above. On introduction for the first time, the hook 12 is introduced along a first partial region of the cardioid into the cardioid and latches in a central region. Therefore the hook 12 is prevented from escaping from the cardioid. In a second actuation, the hook 12 then is moved in the second region of the cardioid, and hence the hook 12 can leave the cardioid again at the upper, free end thereof, as can be seen, for example, in FIG. 6. It is necessary here for the hook 12 to be pivotable about the axis 13 to be able to follow the path of the cardioid.

Figure 10:
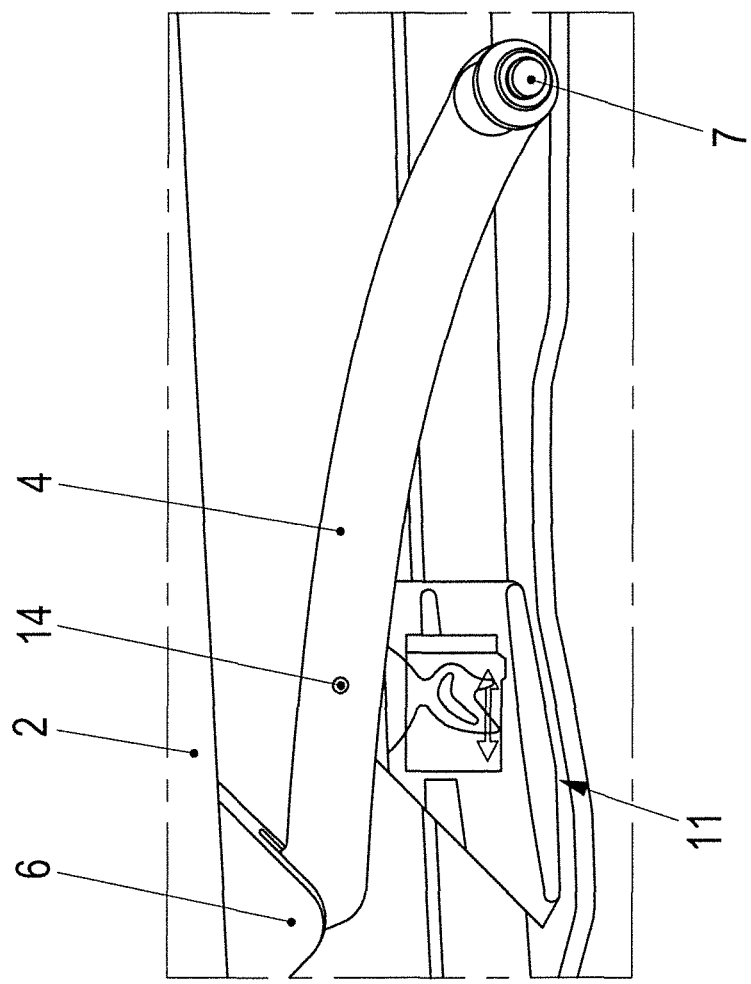
FIG. 10 is a view of a cutout of a wind deflector with a link between the body and the bearing base.
Figure 9:
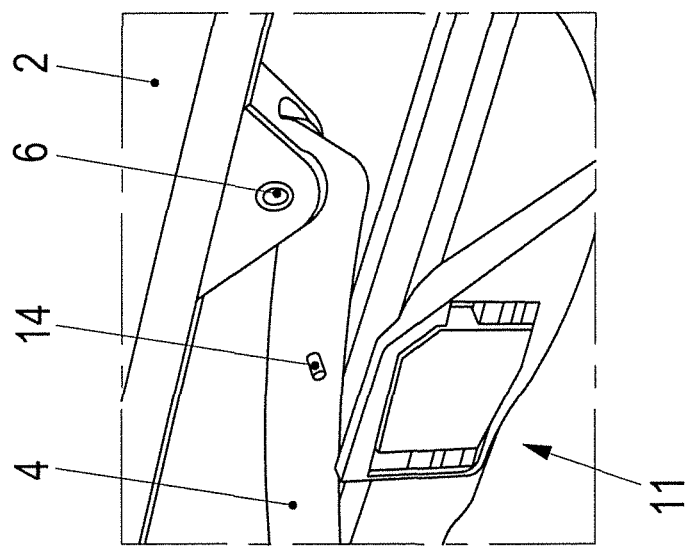
FIG. 9 is a view of a cutout of a wind deflector with a link between the body and the bearing base.

FIGS. 9 and 10 illustrate an alternative configuration in which the hook 12 a projection 14 that is connected fixedly to the link 4. In this embodiment, it is necessary for the cardioid to be shiftable in the lateral direction, such as, for example, in a cassette in a mounting means relating thereto and permitting the lateral movement of the cassette containing the cardioid. Engagement of the projection 14 in the cardioid enables the cardioid to shift correspondingly so that the projection 14 can move away within the slotted guide of the cardioid.

Figure 8:
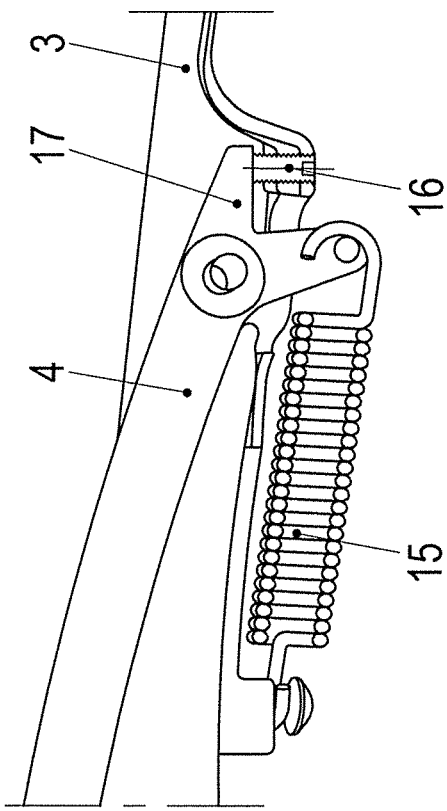
FIG. 8 is a view of a cutout of a wind deflector with a link placed on the bearing base.
Figure 7:
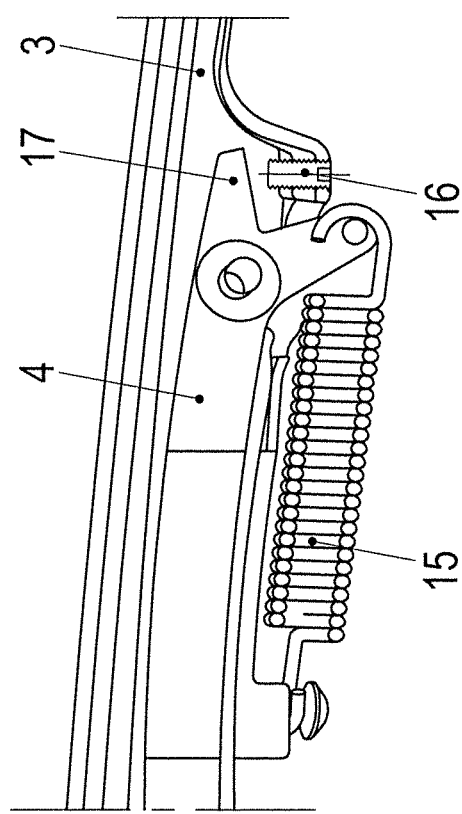
FIG. 7 is a view of a cutout of a wind deflector with a link placed on the bearing base.

FIGS. 7 and 8 show the coupling of the link 4 to the bearing base 3. A spring 15 is coupled both to the bearing base and the link 4 and has a prestress that loads the link 4 into the extended, first position. The spring 15 loads the link 4 in the direction of the first, extended position if the locking mechanism is not latched in the placed-on, second position. First and second stop means 16, 17 are provided for adjusting the maximum pivoting of the link 4 with respect to the bearing base 3. For this purpose, the first stop means 16 is, for example, a grub screw and the second stop 17 is a projection on the link 4. The projection 17 as the second stop is loadable toward the grub screw 16. Adjusting the grub screw 16 determines where the projection stops against the grub screw 16 and hence limits the maximum pivoting angle of the link 4.

At least one element of the wind deflector, in particular the body 2, the bearing base or one of the links 4 may be made from a material that is insert molded with a plastic.

What is claimed is:

1. A wind deflector comprising: a bearing base; a shiftable body that is shiftable relative to the bearing base between a first position, in which the body is spaced from the bearing base, and a second position, in which the body is placed onto the bearing base, two spaced apart links provided between the body and the bearing base, each of the links having a first end articulated to the shiftable body and a second end articulated to the bearing base; a push-push lock disposed and configured for fixing at least one of the links and the body in the second position, and an adjustable stop provided on the bearing base and limiting movement of at least one of the links in the extended position.

2. The wind deflector of claim 1, wherein the lock comprises a cardioid and an engagement structure that engages in the cardioid.

3. The wind deflector of claim 2, wherein the cardioid or the engagement structure is shiftable.

4. A wind deflector comprising: a bearing base; a shiftable body that is shiftable relative to the bearing base between a first position, in which the body is spaced from the bearing base, and a second position, in which the body is placed onto the bearing base, two spaced apart links provided between the body and the bearing base, each of the links having a first end articulated to the shiftable body and a second end articulated to the bearing base; and a push-push lock disposed and configured for fixing at least one of the links and the body in the second position, the lock comprising a cardioid and an engagement structure that engages in the cardioid, the cardioid being positionally fixed, and the engagement structure being pivotable on the link or the body.

5. A wind deflector comprising: a bearing base; a shiftable body that is shiftable relative to the bearing base between a first position, in which the body is spaced from the bearing base, and a second position, in which the body is placed onto the bearing base, two spaced apart links provided between the body and the bearing base, each of the links having a first end articulated to the shiftable body and a second end articulated to the bearing base; and a push-push lock disposed and configured for fixing at least one of the links and the body in the second position, the lock comprising a cardioid and an engagement structure that engages in the cardioid, the cardioid being laterally shiftable, and the engagement structure being positionally fixed on the link or on the body.

6. The wind deflector of claim 1, further comprising a spring braced between the bearing base and at least one link and loading the body into the extended position.

7. The wind deflector of claim 4, further comprising an adjustable stop provided on the bearing base and limiting movement of at least one of the links in the extended position.

* * * * *